(12) United States Patent
Laurell et al.

(10) Patent No.: US 6,929,750 B2
(45) Date of Patent: Aug. 16, 2005

(54) DEVICE AND METHOD FOR SEPARATION

(75) Inventors: Thomas Laurell, Lund (SE); Mats Allers, Lund (SE); Henrik Jönsson, Lund (SE); Hans W. Persson, Lund (SE); Andreas Nilsson, Lund (SE); Filip Tobias Petersson, Lund (SE)

(73) Assignee: Erysave AB, Lund (SE)

( * ) Notice: Subject to any disclaimer, the term of this patent is extended or adjusted under 35 U.S.C. 154(b) by 92 days.

(21) Appl. No.: 10/467,843

(22) PCT Filed: Mar. 11, 2002

(86) PCT No.: PCT/SE02/00428

§ 371 (c)(1),
(2), (4) Date: Aug. 13, 2003

(87) PCT Pub. No.: WO02/072235

PCT Pub. Date: Sep. 19, 2002

(65) Prior Publication Data

US 2004/0069717 A1 Apr. 15, 2004

(30) Foreign Application Priority Data

Mar. 9, 2001 (SE) .............................. 0100819

(51) Int. Cl.⁷ .............................. B01D 43/00; B01J 8/16
(52) U.S. Cl. .................... 210/708; 210/748; 210/95; 209/155; 422/128; 204/158.2
(58) Field of Search ................................ 210/748, 708, 210/767, 95; 209/155; 422/20, 128; 204/157.15, 158.2, 193

(56) References Cited

U.S. PATENT DOCUMENTS 5,085,783 A * 2/1992 Feke et al. ............... 210/748
5,164,094 A   11/1992 Stuckart
5,626,767 A * 5/1997 Trampler et al. ............ 210/748
5,803,270 A * 9/1998 Brodeur ..................... 209/155
6,649,069 B2 * 11/2003 DeAngelis .................. 210/748
2002/0154571 A1 * 10/2002 Cefai et al. ................. 367/13

FOREIGN PATENT DOCUMENTS

| EP | 0773055 | 5/2003 |
| JP | 11-197491 A * | 7/1999 |
| WO | WO 9850133 | 11/1998 |
| WO | WO 0004978 | 2/2000 |

OTHER PUBLICATIONS

IBM Technical Disclosure Bulletin, vol. 25, No. 1, Jun. 1982, H.W. Curtis et al, "Ultrasonic Continuous Flow Plasmaheresis Separator" p. 192–p. 193.

* cited by examiner

Primary Examiner—Frank M. Lawrence
(74) Attorney, Agent, or Firm—Ladas & Parry LLP

(57) ABSTRACT

The present invention provides a device and a method for separating particles from fluids using ultrasound, laminar flow, and stationary wave effects comprising a microtechnology channel system with an integrated branching point or branching fork, and a single ultrasound source. One of the characteristics of the invention is that the single ultrasound source, which generates the standing waves, excites the complete structure including the channel system. No special reflectors or the like are needed. Extremely thin dividers can separate the flow, thereby enhancing the effectiveness of the device. The device could be manufactured in silicon and the ultrasound energy could preferably be delivered by a piezoelectric element.

43 Claims, 22 Drawing Sheets

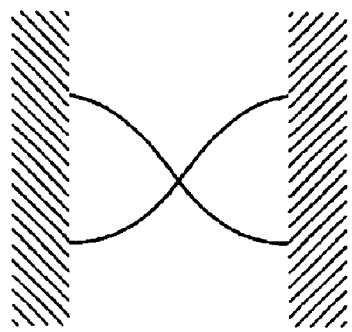
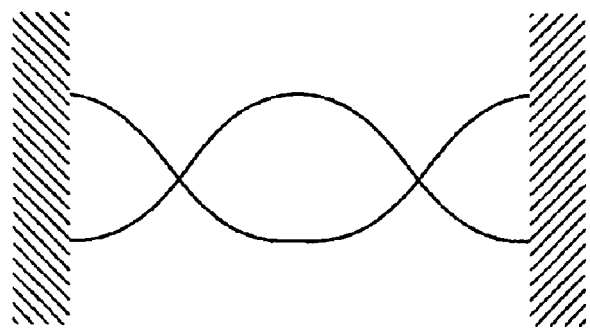
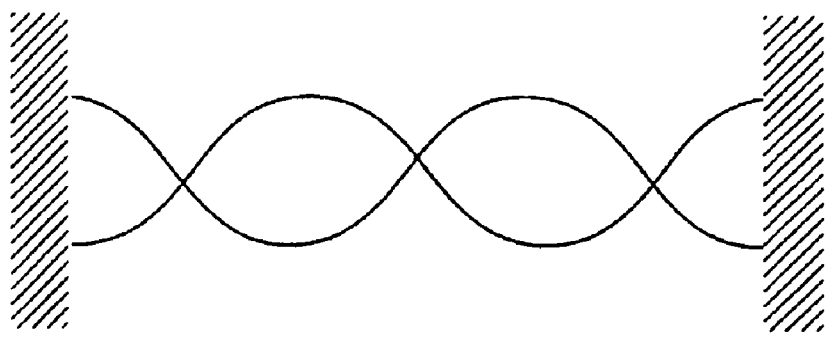
Fig. 7

DEVICE AND METHOD FOR SEPARATION

FIELD OF THE INVENTION

The present invention relates to a device and a method for separating a fluid containing suspended particles into fractions of higher and lower concentration of said suspended particles using ultrasonic standing waves and microtechnology.

STATE OF THE ART

It is known that when particles in a fluid are subjected to an acoustic standing wave field, the particles are displaced to locations at, or in relation to the standing wave nodes. A number of attempts to use ultrasound standing wave field for the manipulation or separation are known.

In WO 00/04978 is described a device for performing the manipulation of particles suspended in a fluid. It comprises a duct for the flow of a fluid in which particles are suspended, and an acoustic transducer and a reflector for establishing an acoustic standing wave field across the width of said duct, the spacing between the transducer and reflector being 300 μm or less.

In an abstract to the 4$^{th}$ annual European conference on micro & nanoscale technologies for the biosciences (NanoTech 2000), Hawkes and Coakley describes a "force field particle filter, combining laminar flow and ultrasound standing waves" with an acoustic path length at right angles to the flow of 0.25 mm.

In WO 98/50133 is described a device for performing the manipulation of particles suspended in a fluid. It comprises a duct for the flow of a fluid, in which particles are suspended, said duct having means for establishing an acoustic standing wave field so that the particles are displaced to form parallel bands. The duct includes an expansion in width.

In IBM, technical disclosure bulletin vol. 25, No. 1, June 1982, page 192/193 is disclosed an ultrasonic continuous flow plasmapheresis separator comprising two orthogonally mounted ultrasound transducers with one reflector each and a volume between where a dilute suspension is subjected to an acoustic standing wave field.

In JP 06241977 A is described a fine particle measuring instrument that uses a standing ultrasonic wave with a node at the centre of a flow cell to centre and concentrate fine particles.

In EP 0 773 055 A2 and A3 is described a method and an apparatus for handling particles by an acoustic radiation force. The apparatus comprises a chamber for accommodating a fluid containing the particles to be concentrated, filtered or arranged, and a plurality of ultrasound sources disposed to make direct or indirect contact with the fluid. The apparatus also comprises a control device for controlling said ultrasound sources to generate an ultrasound beam obtained by superimposing ultrasound beams from said ultrasound sources on one another, said beams each having a specific intensity, a specific frequency and a specific phase.

In WO 93/19367 A2 and A3 is described a method and an apparatus for particle aggregation, said apparatus comprising a tube for containing of a sample of a liquid, and an ultrasonic transducer arranged to generate a standing wave ultrasound field transverse to the tube. The standing wave exhibiting a progressive change in pressure amplitude transverse to the tube, so that, in use of the apparatus, particles in suspension are displaced transversely of the tube to one or more predetermined regions. After termination of exposure to the standing wave particles are allowed to settle and can then be inspected. Appreciated use of the apparatus includes carrying out immuno-agglutination assays. The document is based on U.S. Pat. Nos. 5,665,605 and 5,912,182.

In JP 07 047259 A is described an apparatus for transporting fine particles in fluid with ultrasonic waves. The apparatus comprises a multitude of ultrasonic wave generating elements two-dimensionally arranged on two flat plates. Between the plates a solution can be deposited.

SUMMARY OF THE INVENTION

The present invention provides a device and a method for separating particles from fluids using ultrasound, laminar flow, and stationary wave effects comprising microtechnology channels formed in the surface portion of a plate, having integrated branching points or branching forks, and an ultrasound source arranged in close contact to an opposing surface of said plate.

Standing waves are generated in the channels so that particles suspended in the fluid are brought into certain lamina of said fluid, and that one or more lamina are formed devoid of particles, or are formed carrying particles of different properties than the first mentioned ones. Said laminae are thus arranged perpendicular to said plate, this is important because the branching of a channel must take place within the plate, so that a connection with another channel can take place also within the same plate. The advantages of this will be obvious below.

One of the characteristics of the invention is that the ultrasound source is arranged in perpendicular contact with the plate, conveying ultrasound energy in a direction that is perpendicular the plate. The inventors have tested and proved that in the present invention, as a result of the dimensions of the channels and the properties of the plate and the ultrasound transmitter, a standing wave is generated that reaches from one side wall of a channel to the opposing side wall of the same channel. It would normally be expected that such an arrangement would generate (only) a standing wave reaching from a bottom wall to a top wall of said channel, continuing in a direction of the original energy flow.

The inventors have also realised the great importance of this idea. Because, according to the invention, the ultrasound source now do not have to be a part of the plane or layer where the channels reside, and space becomes available for packing more channels into a limited space, greatly enhancing the possibilities of manufacturing devices with a multitude of parallel channels providing high capacity particle separation. A high degree of particle separation could also easily be provided by a serial arrangement of separation units, as will be further explained below. The capability of high yield parallel and serial processing of a fluid using ultrasound is thus a central part and consequence of the inventive concept.

The above is possible because the channels and branching points are formed in a plate comprising one piece of material or in a few pieces of material closely bonded together. No special reflectors or the like are used. It may also be possible to use more than one ultrasound source. Thin dividers are arranged to separate the laminar flows after the branching points, thereby enhancing the effectiveness of the device. The device is preferably manufactured using silicon technology benefiting from the possibility of small precise dimensions, and the ultrasound energy could preferably be delivered by a piezoelectric element, which in turn could be driven from a control unit capable of delivering electrical energy of certain shape, frequency and power.

The invention is defined in the accompanying claim 1, while preferred embodiments are set forth in the dependent claims.

BRIEF DESCRIPTION OF THE DRAWINGS

The invention will be described below with reference to the accompanying drawings, in which:

FIG. 7 shows standing waves in the space between two walls;

DETAILED DESCRIPTION OF PREFERRED EMBODIMENTS

Figure 1:
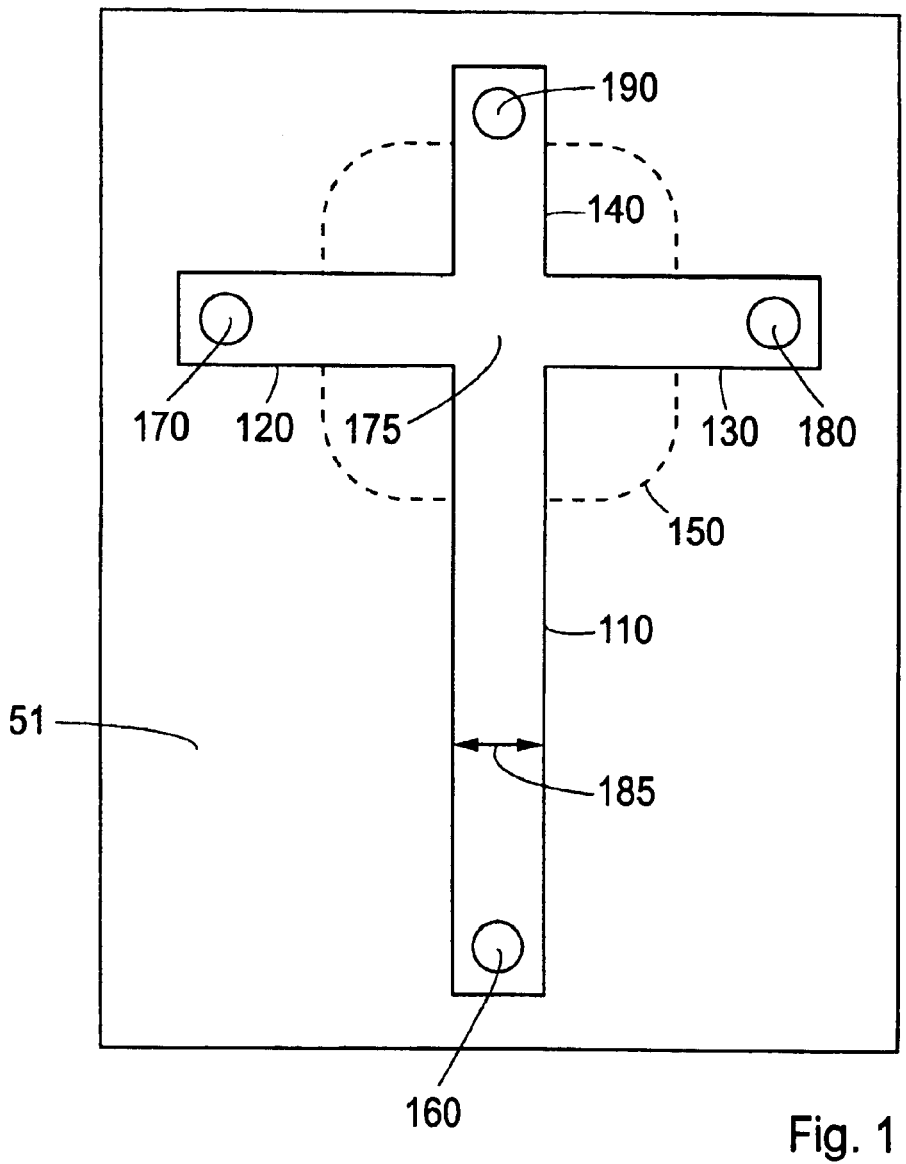
FIG. 1 shows a top view of a cross channel system arrangement.
Figure 2:
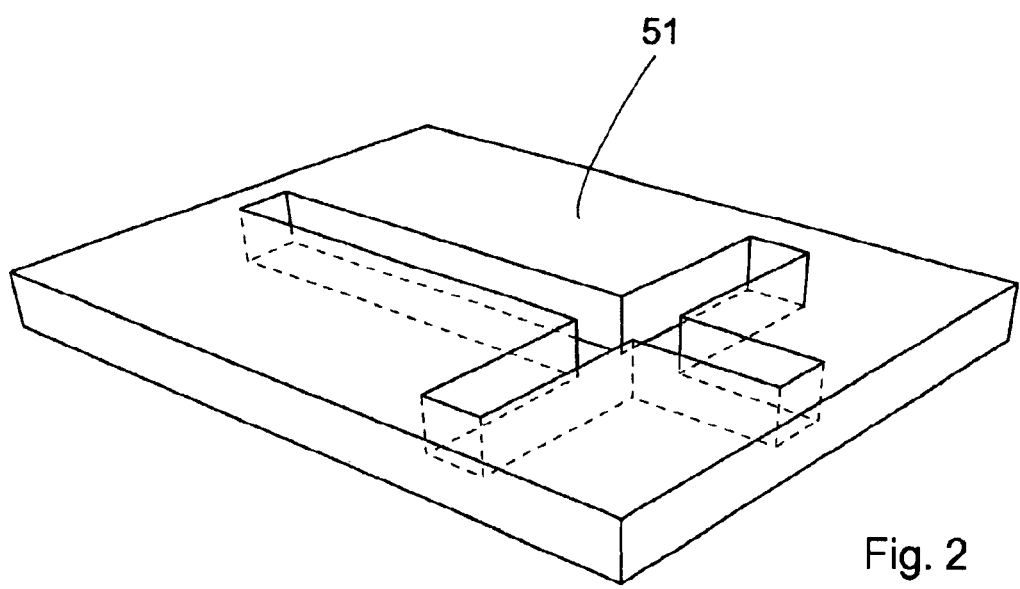
FIG. 2 shows a perspective view of the object in FIG. 1.
Figure 8:
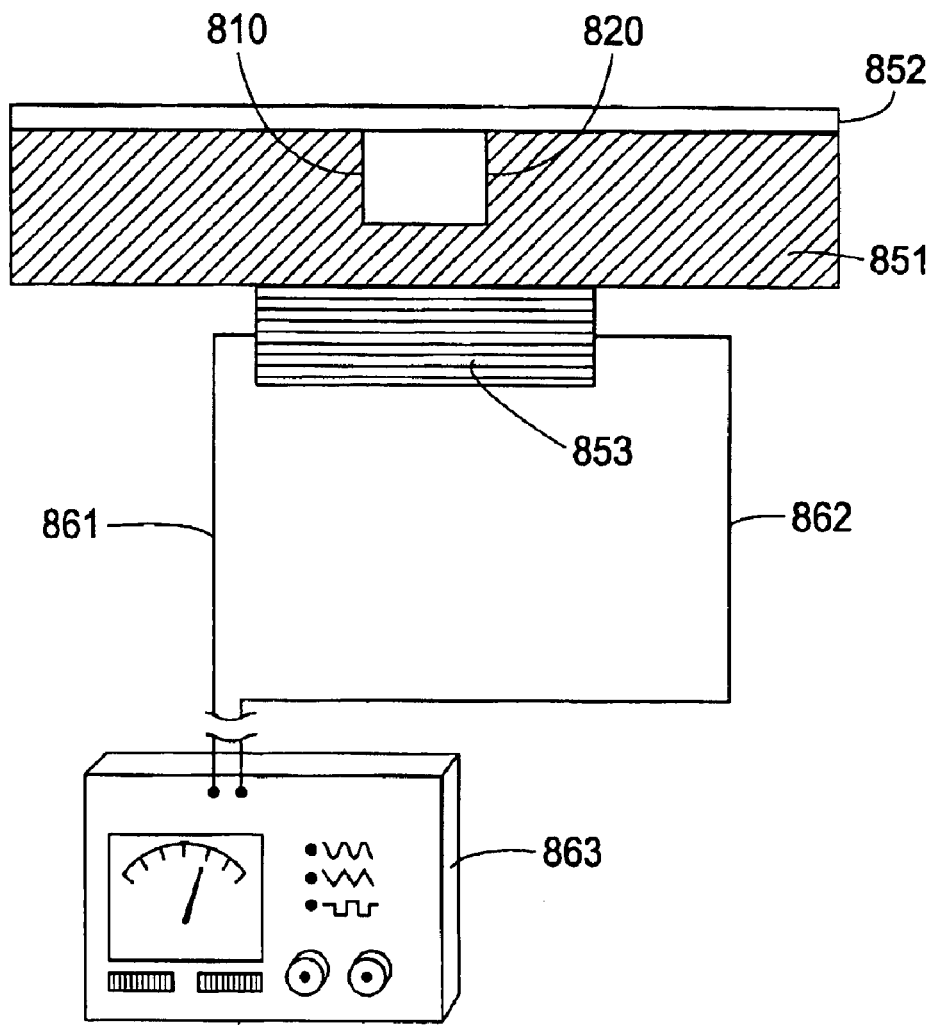
FIG. 8 shows a cross section view of the device.

Referring to FIGS. 1, 2, and 8, one embodiment of the invention comprises a plate 51,851, with an integrated channel system, with a base stem 110 and a left arm 120, a right arm 130 and a central arm 140. The walls of the base stem 810, 820 are essentially perpendicular to the plate 51 and parallel or near parallel to each other, and to the flow, which is a prerequisite for the establishment of standing waves across the channel along its entire depth and length, see below.

At the back of the plate 51, means for delivering ultrasound energy to the plate is arranged in the form of a piezoelectric element 150, 853. The device will function as follows:

A fluid with suspended particles entering the base stem 110 at the inlet 160 will flow towards the branching point 175 because of an arranged pressure gradient, which gradient could be created by e.g. a suction pump, a pressure pump, a syringe or by gravity. By controlling the frequency of the ultrasound and use of certain frequencies suitable to the dimensions of the base stem 110, particularly the width 185 of said stem 110, a stationary wave pattern is formed in the fluid inside said stem 110. Especially there will form a stationary wave pattern orthogonal to the direction of the flow between a left 810 and a right 820 side wall of the base stem 110. Pressure nodes will form in greater numbers in the middle part of the channel than at the walls, where pressure antinodes will form. During said flow, particles in the fluid will tend to accumulate in nodes of said stationary wave-pattern, or in certain layers in relation to the nodes depending on the particles' density/densities/acoustic impedance relative to the surrounding fluid. Particles with a higher density than said surrounding fluid will tend to accumulate in the nodes, whereas particles with a density lower than the surrounding fluid will tend to accumulate in the antinodes. The layers of fluid discussed in the following are the layers parallel to the sidewalls 810, 820 of the base stem 110.

Figure 6:
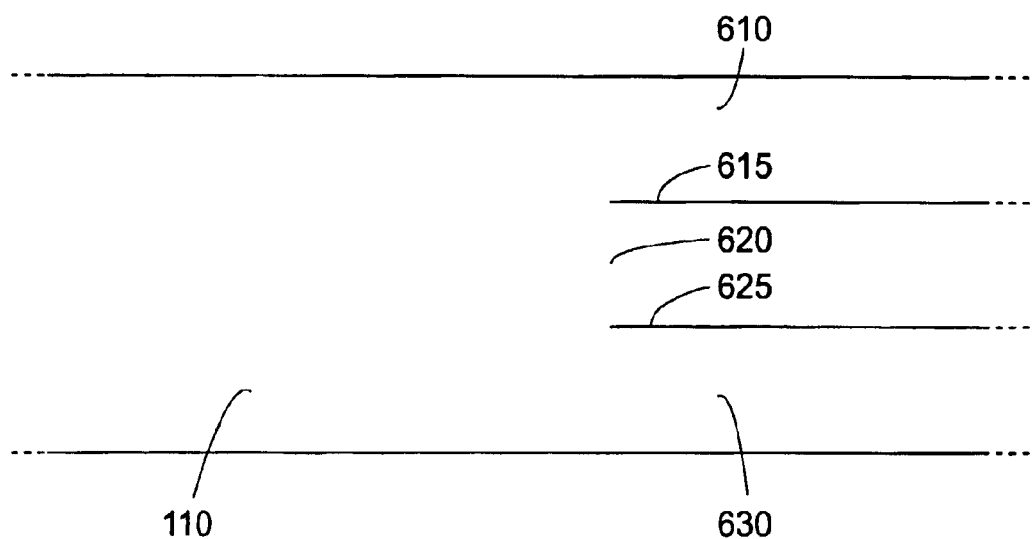
FIG. 6 shows a detail top view of a parallel arrangement branching point.

Depending on the density/acoustic impedance, size and weight of the particles, certain patterns of accumulations of particles will be formed. This is an advantage when separating out particles of a certain weight and/or size from a medium containing a spectrum of particles of different density/acoustic impedance. Generally, particles having a density higher than the density of the surrounding fluid, accumulates in the nodes, and particles having a density lower than the fluid without particles, accumulate in the antinodes. By providing a branching fork with two side branches or arms and one central branch or arm 140 as shown in FIGS. 1, 6 or 8, it is possible to separate out said particles. The post-branch point arms or channels are preferably arranged with spacing adapted to the wavelength, i.e., a centre to centre distance of approximately ⅜ of a wavelength.

Figure 9:
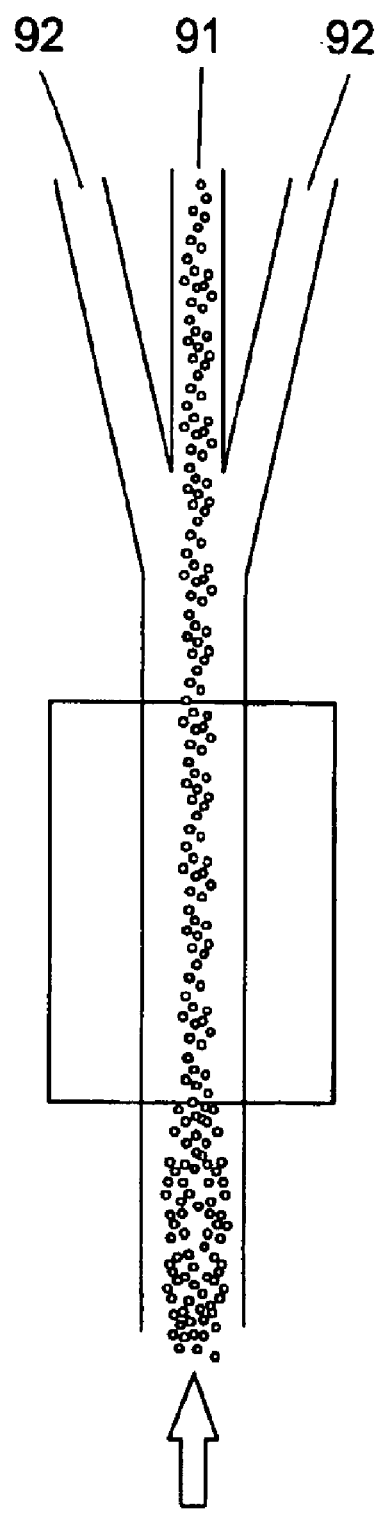
FIG. 9 shows schematically separation using one-node standing wave.
Figure 10:
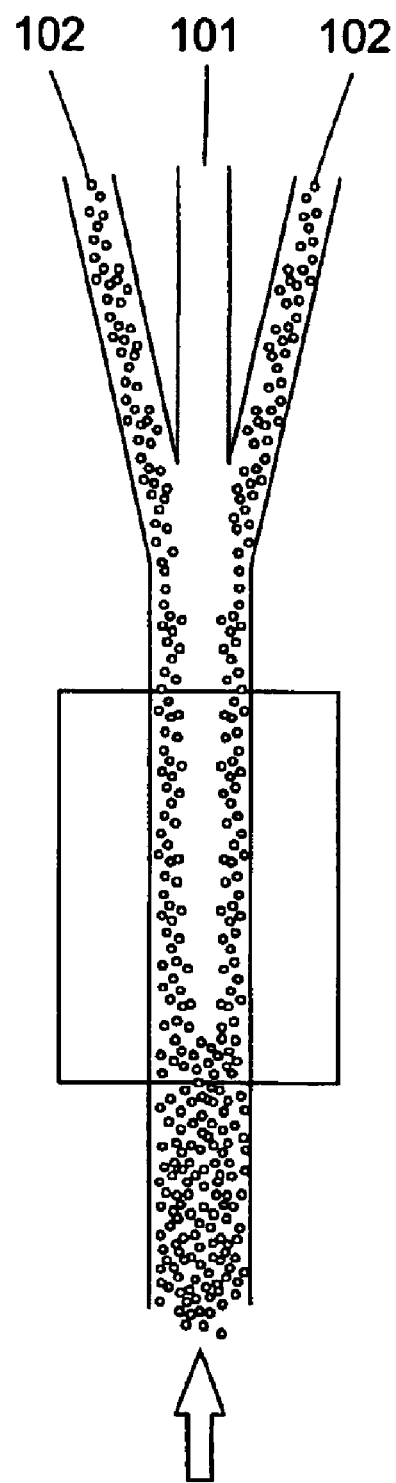
FIG. 10 shows schematically separation using two-node standing wave.

Depending on the resonance conditions, confer FIG. 7, different results of the above will be obtained. For a single node condition, the result of the above is that the layers of fluid near the walls of the base stem 110 will contain a decreasing concentration of high density particles as the fluid flows along said stem 110 towards the branching point 175. At said branching point 175, fluid that mainly originates from the central parts of the fluid-stream in the stem 110 will, due to laminar flow, continue its movement straight ahead and enter the central arm 140. Fluid originating from the fluid-stream appearing near the walls of the stem 110, will deflect into the left arm 120 (from the left wall) and into the right arm (from the right wall). Fractions of fluid containing a low concentration of high-density particles can then be collected at the left outlet 170 and the right outlet 180. The fraction of fluid containing a high concentration of high-density particles can be collected at the top outlet 190. In FIG. 9 is shown how a number of high density particles (higher density than surrounding fluid) accumulates in a central division or channel with a central outlet 91, whereas fluid with a low or zero concentration of said particles flows out at the lateral divisions and outlets 92. As a comparison, FIG. 10 shows one way of using a two-node standing wave pattern to move the particles so that they can be collected at two lateral divisions provided with outlets 102. Fluid with a low or zero concentration of said particles flows out at the central division and outlet 101. A similar effect could also be achieved using five divisions or channels, where the most lateral channels and the central channel collect fluid with low or zero concentration of high density particles, and the other two channels collect fluid with high concentration of said particles, i.e. n=3 below.

By controling the frequency of the uitrasound that creates the standing wave field it is possible to generate a standing wave between the side walls of the base stem 110 with a standing wave length 0.5, 1.5, 2.5 etc. wavelengths, i.e., n times 0.5 wavelengths, n-1, 3. 5, 7 . . . cf. FIG. 7. A device according to the invention making use of the invention's ability to separate particles into the nodes and entinories could therefore have a number of channels after the branching point corresponding to the number of nodes plus the number of aritinodes in the standing wave field. For example, frequencies having 0.5, 1.5 and 2.5 wavelengths across the base stem 110 could have 3, 5 and 7 channels correspondingly.

Preferred embodiments of the invention therefore include means for controlling the frequency of the ultrasound generating means. In FIG. 8 is shown how a control unit 863 (shown in a different scale) can be connected to the piezoelectric element 853. Said control unit 863 is capable of delivering electrical energy to said element 853. Said electrical energy is controllable with regard to waveform, frequency and power, where said waveform is controllable to be one of, but not limited to sinus wave, triangular wave or square wave.

Other embodiments of the invention include bifurcation and "trifurcation" of different shape, integrated on the same piece of material, and with the overall purpose to divide the laminar flow of fluid.

In FIG. 6 is shown a detail of another embodiment where the branching point comprises the branching of the base stem 110 directly into three parallel arms 610, 620, 630 divided by thin dividing walls. By the use of the techniques described below it is possible to arrange these thin walls with a thickness of down to 1 µm and even lower. Thin walls will give better performance due to better preservation of the laminar flow profile across the full channel width.

Figure 14:
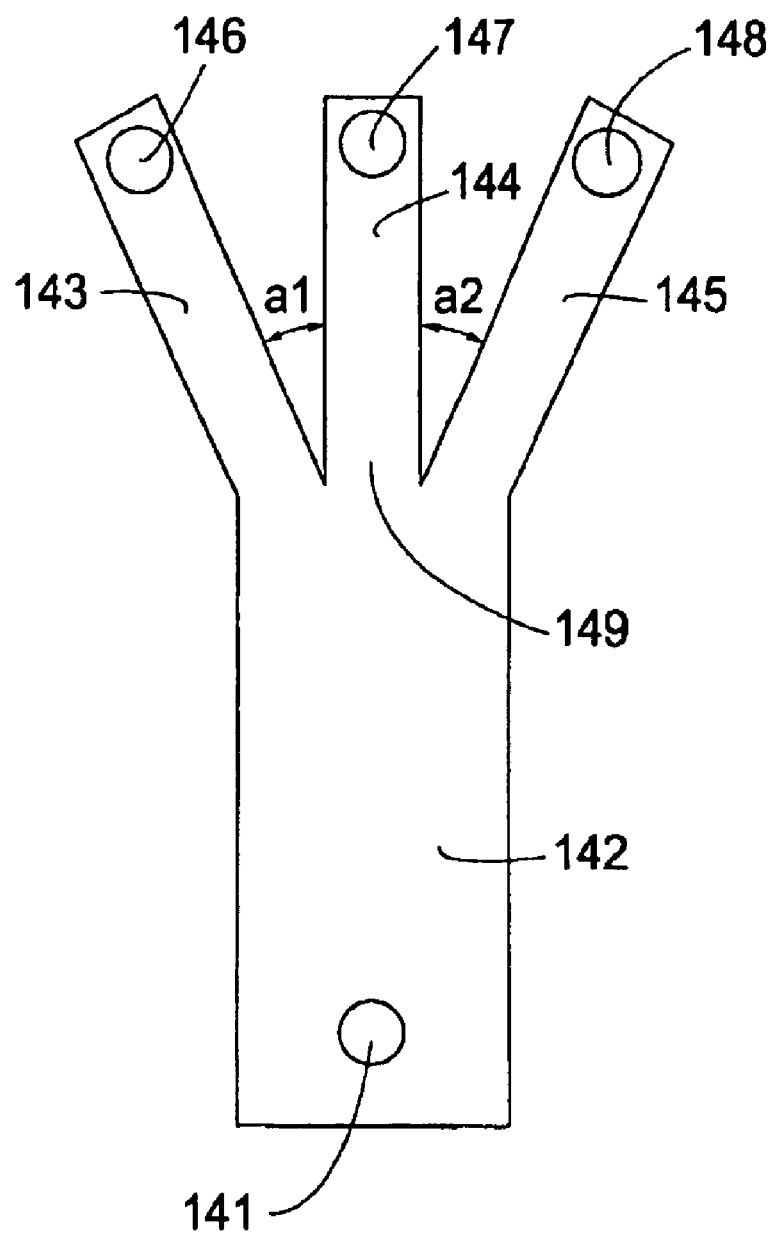
FIG. 14 shows a top view of an embodiment with labelled branching angles.

FIG. 14 shows an embodiment with a left branching angle α1 between a left arm 143 and a central arm 144 and a right branching angle α2 between said central arm 144 and a right arm 145. By varying the angles α1 and α2 it is possible to optimise certain factors such as e.g. the degree of particle concentration. However, certain angles can be difficult to manufacture with certain manufacturing processes. Angles between 0 and 90 degrees show good ability to separate flow.

Figure 3:
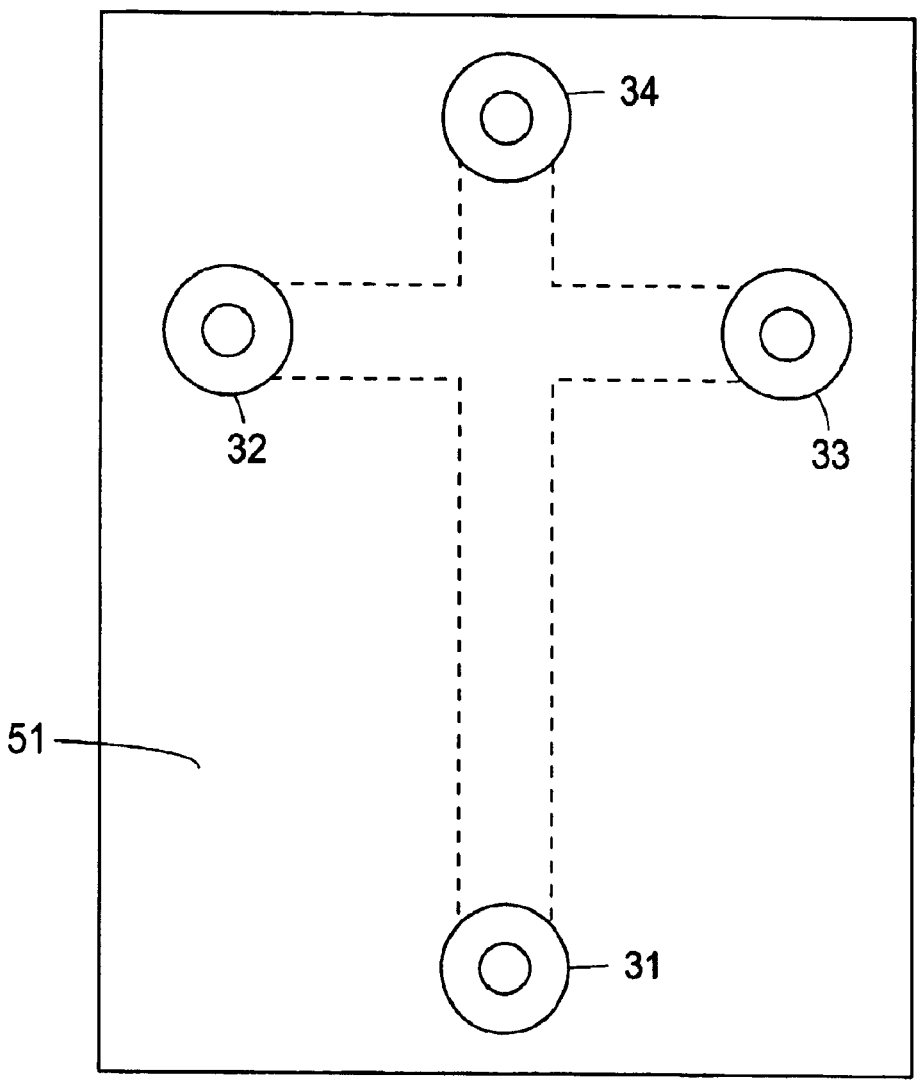
FIG. 3 shows a bottom view of the object in FIG. 1.

In FIG. 3, which shows the device from beneath, are shown the connections 31–34 to the inlet 160 and to the outlets 170, 180, 190 from FIG. 1. The piezoelectric element is not shown for the sake of clarity.

Figure 4:
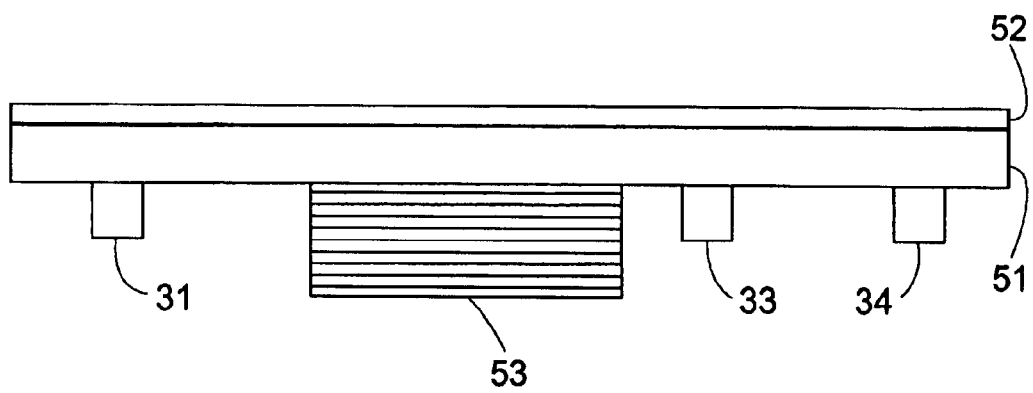
FIG. 4 shows a side view of the object in FIG. 1.
Figure 5:
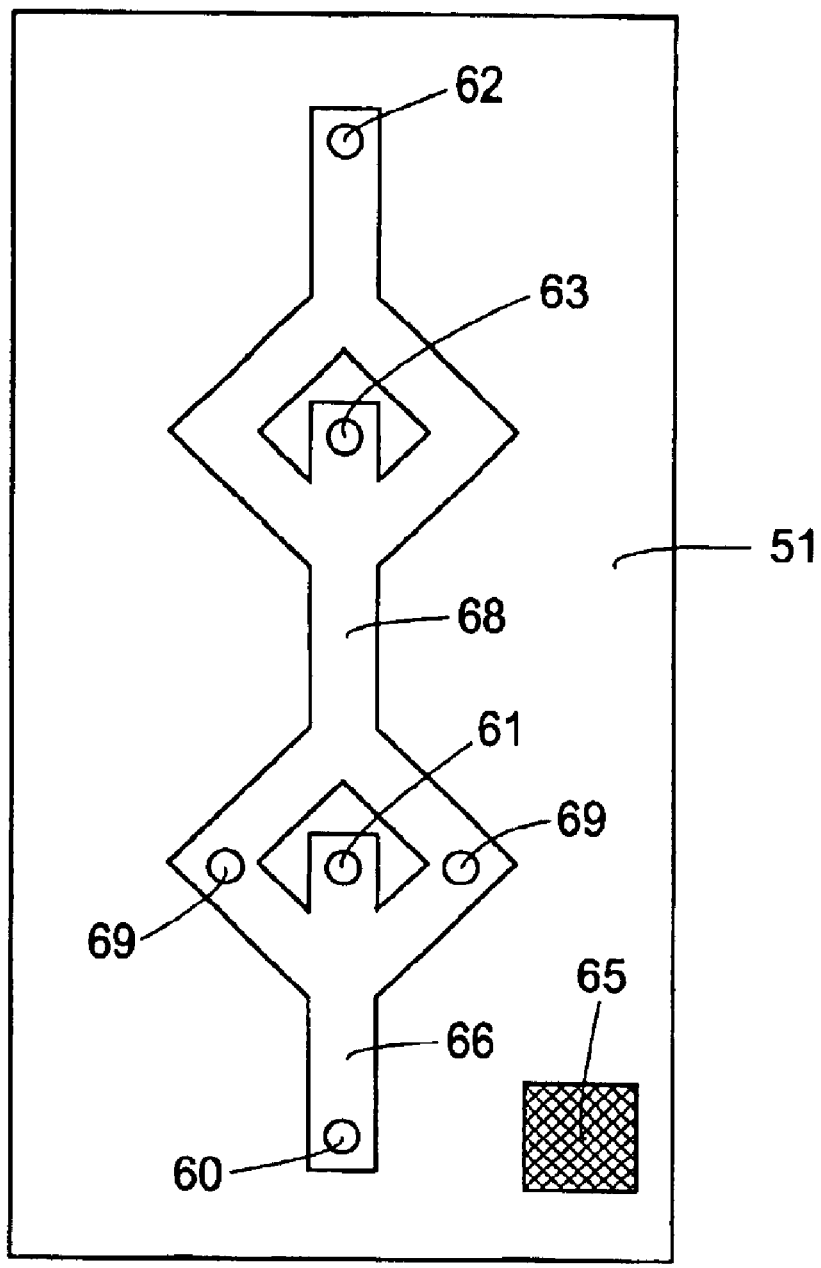
FIG. 5 shows a top view of a repeated arrangement.

In FIG. 4 the device is shown from the side. The device preferably comprises two layers, one layer 51 including the channel system, made e.g. of silicon, and one sealing layer 52 made of e.g. glass which makes it possible to visually inspect the process. The sealing glass layer could preferably be bonded with known techniques to the base layer 51. The piezoelectric element 53 is arranged in acoustic contact with the base layer 51.

In FIGS. 5, 11, 12, and 13 arrangements are shown where certain effects can be achieved through a consecutive or serial use of repeated structures. For example, high and low density particles can be separated using the arrangement in FIG. 5. (high and low density indicate merely the density relatively to the surrounding fluid). Here, fluid is entered at a main inlet 60. If a one-node resonance condition is present, fluid with high concentration of high-density particles will accumulate at outlet 61. Fluid with low concentration of high-density particles together with high concentration of low-density particles will accumulate at outlet 62, and fluid with intermediate concentration of high-density particles will accumulate at outlet 63. A piezoelectric element 65 is arranged in acoustic contact with the common supporting structure, giving rise to standing wave fields in channels with appropriate dimensions, i.e. the channel parts 66 and 68. To compensate for fluid loss, inlets 69 are provided for adding pure fluid without particles. The inlets could also be used for cleaning of the system.

Parallel arrangements of single or serial structures according to FIGS. 5, 11, 12, and 13 can easily be achieved. Channel systems according to embodiments of the invention could e.g. repeatedly and inter-connectedly be arranged, filling the area of the plate, which plate can comprise e.g., a silicon wafer or other area sheets or discs of other materials such as e.g. plastics. Parallel arrangements will add capacity, i.e. more fluid volume can be processed per time interval.

Figure 11:
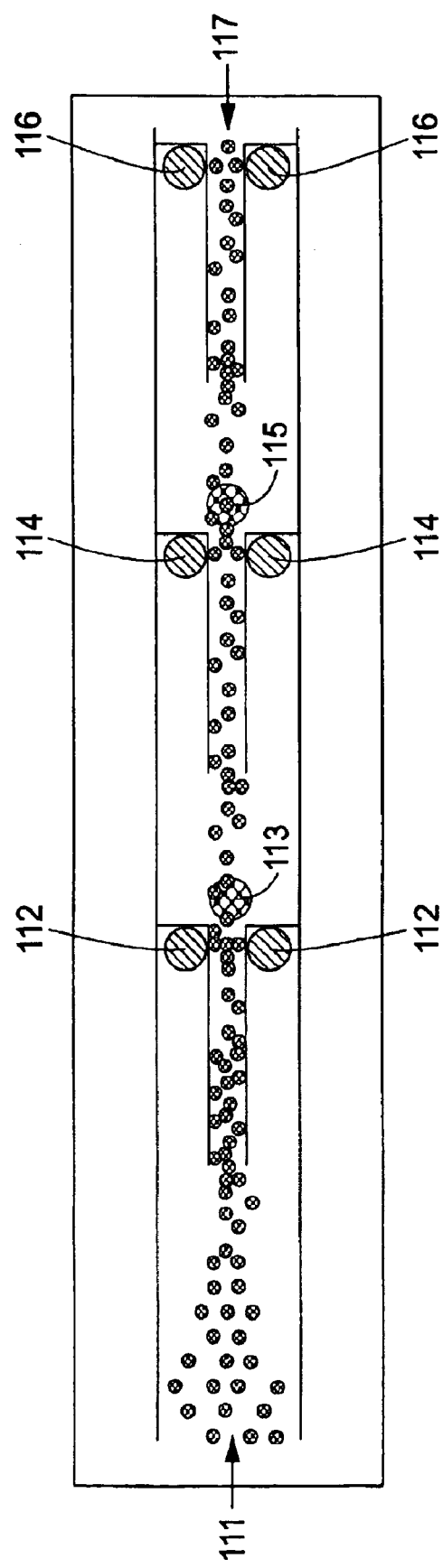
FIG. 11 shows schematically a one-node three-step serial wash.

FIG. 11 shows schematically a one-node three-step serial washer. Contaminated fluid with particles of interest to save (e.g. red blood cells) enters at inlet 111. Contaminated fluid with low or zero concentration of particles leaves at outlets 112. Particles continue to flow, passing inlet 113 which adds clean fluid to the particles and some still remaining contaminants will become more diluted. Separation will be repeated in a second step where contaminated fluid with low or zero concentration of particles leaves at outlets 114. Particles continue to flow, passing inlet 115, which adds clean fluid to the particles and if still some remaining contaminants, these will become even more diluted. Separation will then be repeated in a third step, and particles suspended in now very clean fluid will leave at outlet 117.

Figure 12:
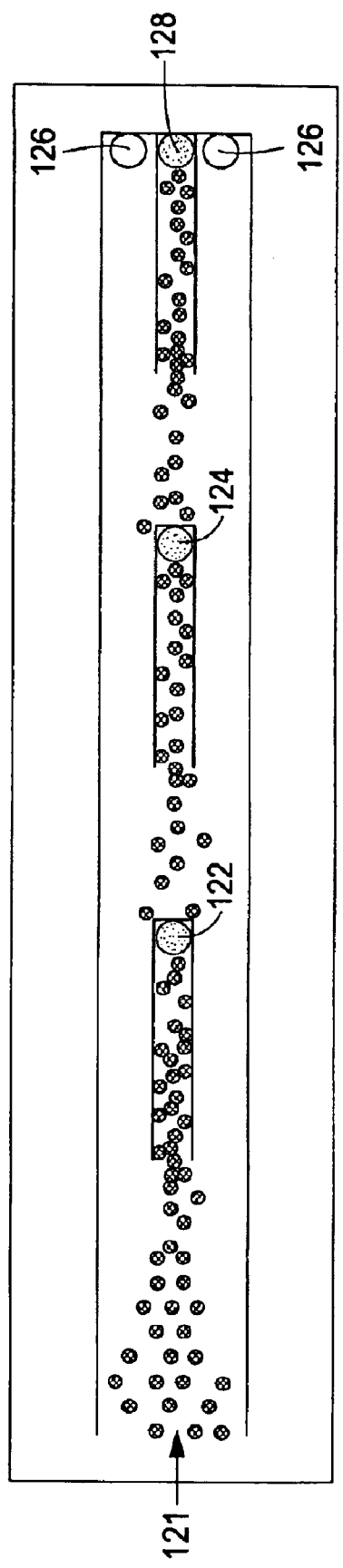
FIG. 12 shows schematically a one-node three-step concentrator.

FIG. 12 shows schematically a one-node three-step serial concentrator. Contaminated fluid with particles of interest to save (e.g. red blood cells) enters at inlet 121. Particles are concentrated at outlets 122, 124 and 128. Contaminated fluid is removed at outlets 126.

Figure 13:
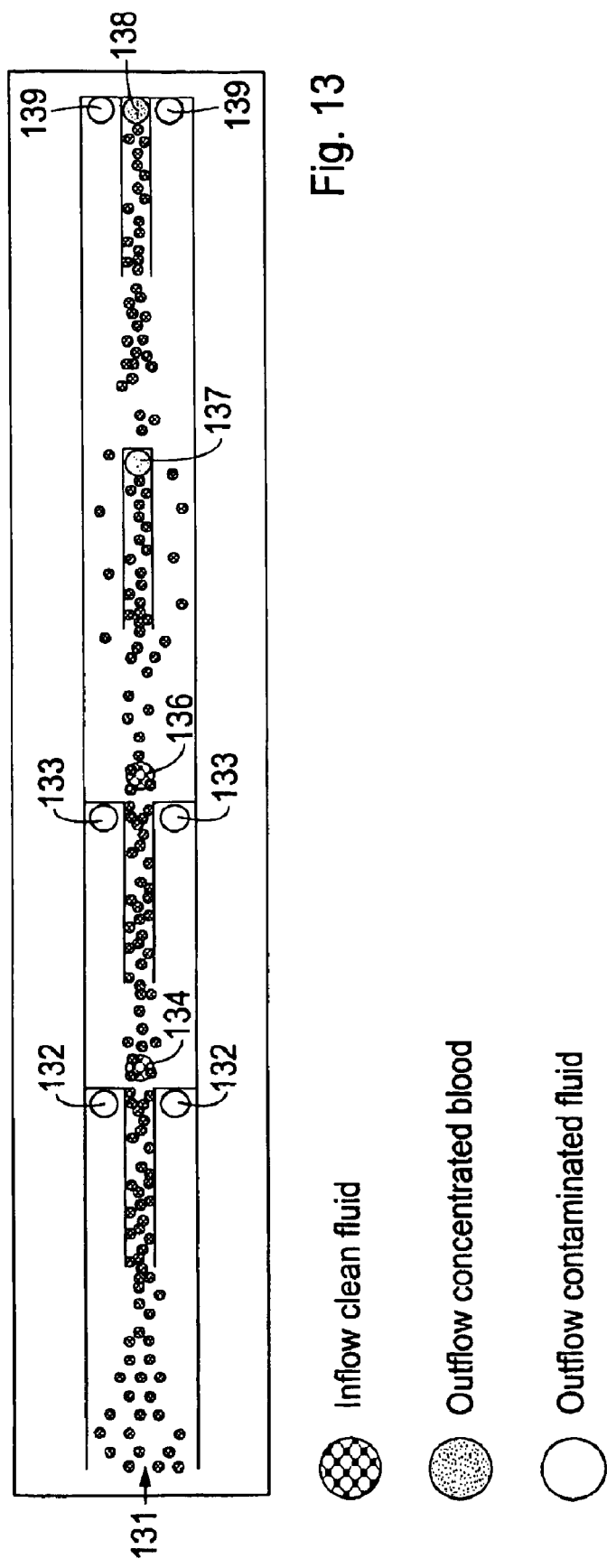
FIG. 13 shows schematically a one-node four-step integrated wash and concentrator.

FIG. 13 shows schematically a one-node four-step integrated washer and concentrator. Contaminated fluid with particles of interest to save (e.g. red blood cells) enters at inlet 131. Contaminated fluid with low or zero concentration of said particles leaves at outlets 132. Clean fluid is added at inlet 134. In a second step, (less) contaminated fluid with low or zero concentration of particles leaves at outlets 133. Clean fluid is added at inlet 136. In steps 3 and 4 particles are concentrated and removed through outlets 137 and 138. Excess fluid is removed through outlets 139.

Returning now to FIG. 1, the channel system, including the base stem 110 and the branching point, is preferably integrated on a single piece of homogenous material 51 in FIG. 4. This entails the advantage of ease to repeat a number of channel systems thereby easily increasing the capacity of a separation apparatus making use of the invention.

Preferred embodiments include embodiments with channel systems integrated with a single substrate or deposited on a substrate by a continuous series of compatible processes.

The device according to the present invention can be manufactured for example in silicon. The requirement to make the walls of the base stem (810, 820) essentially perpendicular to the plate and parallel or near parallel to each other is easily fulfilled by using silicon of a <110> crystal structure and well known etching techniques. The desired channel wall structure described may also be realised by deep reactive ion etching, DRIE.

It is also possible to form the layers in plastic materials, for instance by using a silicon matrix. Many plastics have good chemical properties. The silicon layer structure can be produced by means of well-known technologies. Channels and cavities can be produced by means of anisotropic etching or plasma etching techniques. The silicon layer may be protected against etching by an oxide layer that is by forming a $SiO_2$ layer. Patterns may be arranged in the $SiO_2$ layer by means of lithographic technologies. Also, etching may be selectively stopped by doping the silicon and using p.n. etch stop or other etch stop techniques. Since all these process steps are well known in the art they are not described in detail here.

The above described technology is also suitable for producing a matrix or mould for moulding or casting devices of the invention in e.g. plastic.

The piezoelectric element providing the mechanical oscillations is preferably of the so-called multi-layer type, but a bimorph piezoceramic element may also be used as well as any other kind of ultrasound generating element with suitable dimensions.

An appreciated application of an embodiment of the invention is in the field of cleaning a patient's blood during surgical operations. The object in this field is to sort out the red blood cells from the contaminated plasma. Contamination could include air bubbles, fat particles, coagulation products and other not desirable biological material. The red cells will thereafter be brought back to the patient's circulation. One disadvantage with prior art in the form of centrifuges is that the red blood cells can become deformed, a disadvantage that is not present with a device according to the present invention.

Depending on the application, the shape and dimensions of the channel, the length of the stem 110 and the arms 120, 130, 140, and the frequency of the ultrasound may vary. In an application for separating out red blood cells from diluted blood recovered from a patient during a surgical operation, the channel is preferably rectangular in cross-section and the stem part of the channel has a width of 700 $\mu$m for a one-node standing wave ultrasound field. Greater widths will be appropriate for standing wave ultrasound fields with more nodes.

The mechanical tolerance of the width of the channel is important. The difference should preferably be less than a few percent of half the wavelength of the frequency used in the material/the fluid concerned.

Figure 15:
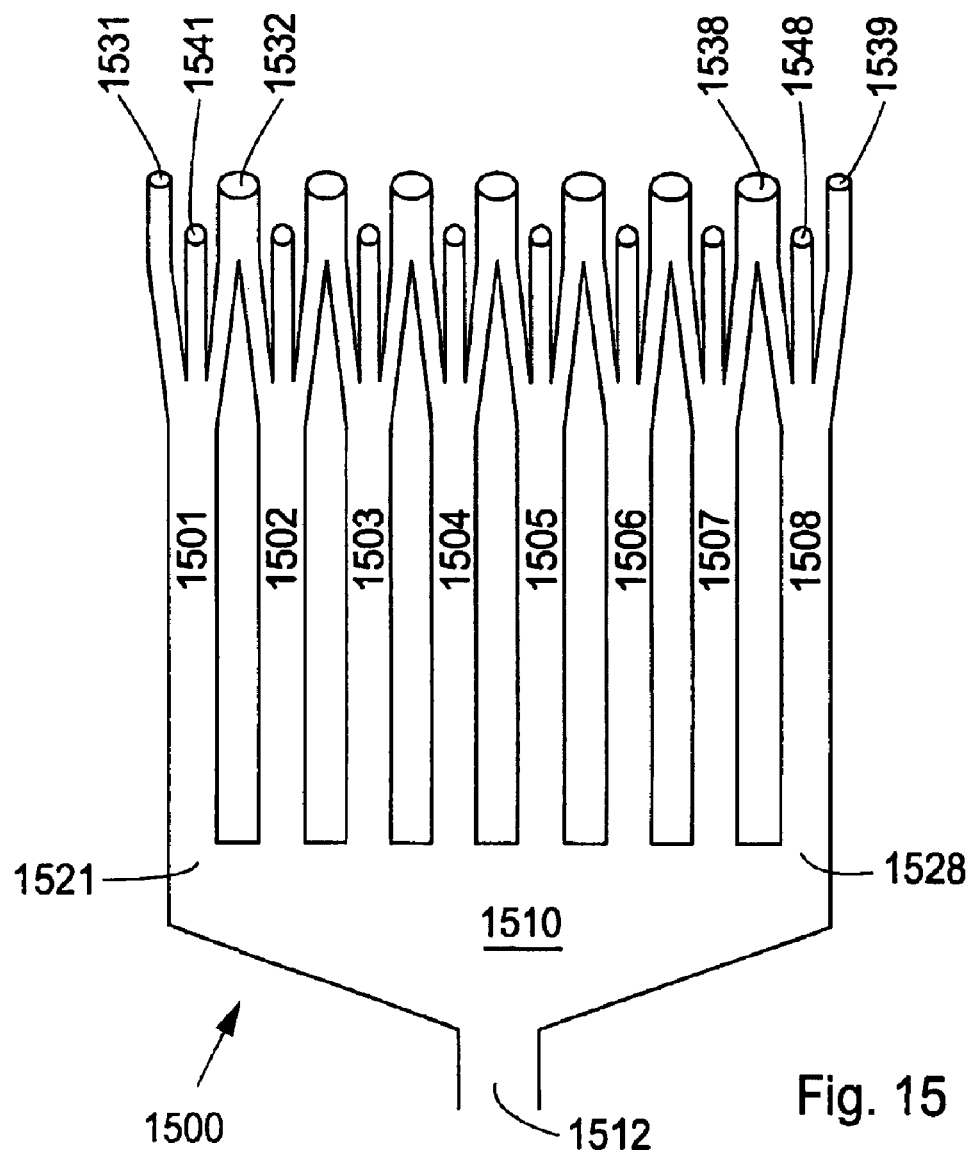
FIG. 15 shows a parallel arrangement of eight channel units.

FIG. 15 shows a separation unit comprising eight channel units 1501–1508, which units are supplied with fluid from a distribution cavity 1510 having one inlet 1512 and eight outlets 1521–1528. Each channel unit 1501–1508 is provided with three outlets, one central outlet 1541 and two lateral outlets. Said lateral outlets are connected in pairs, except for the two most lateral outlets of the separation unit 1500, forming nine intermediate outlets 1531–1539. Said intermediate outlet are connected to a fast collecting cavity (not shown) alternatively to a first collecting manifold (not shown). The central outlets 1541–1548 are connected to a second collecting cavity alternatively to a second collecting manifold (neither shown).

Figure 16:
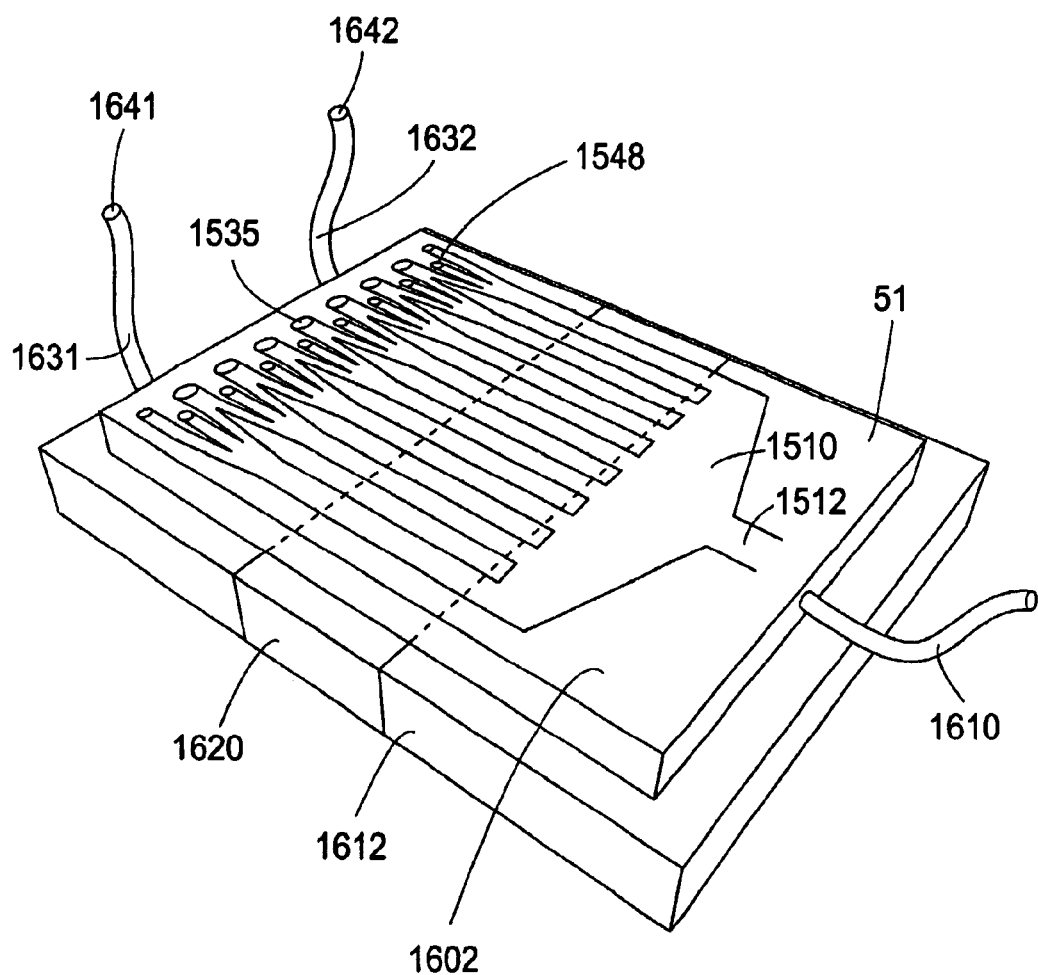
FIG. 16 shows the parallel arrangement of FIG. 15 in perspective.

FIG. 16 shows the separation unit 1500 of FIG. 15 in a perspective view. The plate 1602 in which the separation unit 1500 is formed is arranged on top of an ultrasound source 1620, preferably a piezoelectric element 1620 and a support structure 1612. An inlet tube 1610 is connected to the distribution cavity inlet 1542 to provide an inlet for the fluid connectable to outside tubing.

A first outlet tube 1631 is providing a connection from the nine intermediate outlets 1531–1539 via a first collecting manifold to a free end 1641 of said first outlet tube 1631. A second outlet tube 1632 is providing a connection from the eight central outlets 1541–1548 via a second collecting manifold to a free end 1642 of said second outlet tube 1632.

Figure 17:
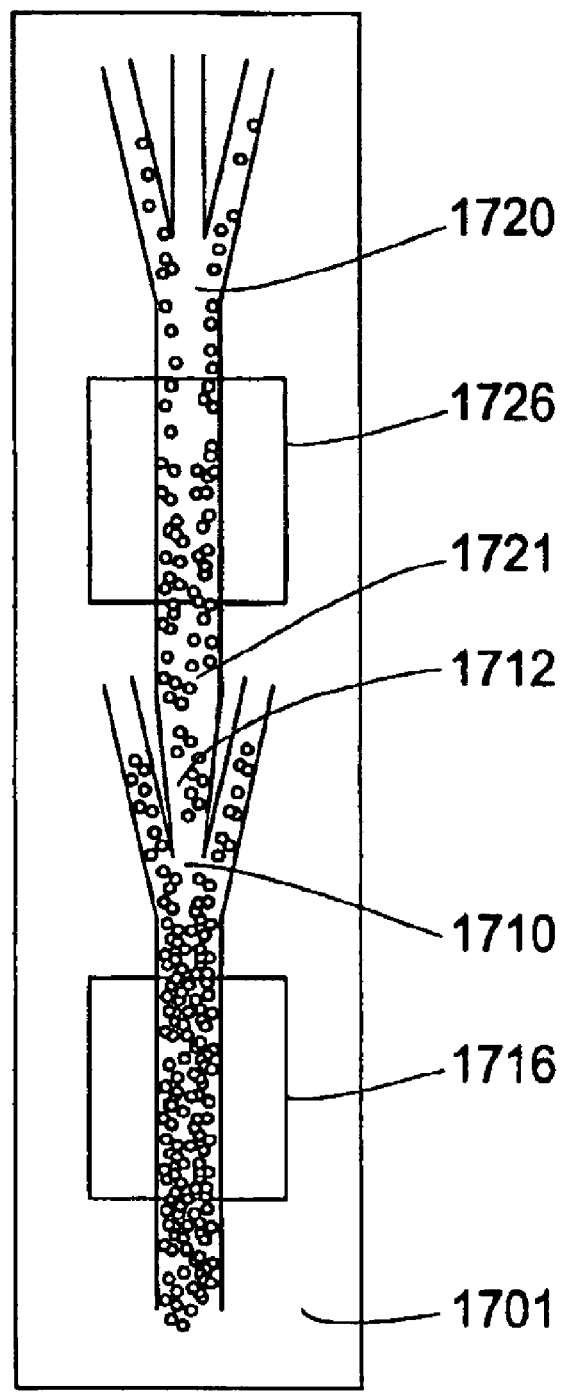
FIG. 17 shows schematically a serial arrangement of two channel units.

FIG. 17 shows a serial arrangement in a plate 1701 of two channel units, devised to increase particle separation from a fluid. A first channel unit 1710 is formed in the plate 1702 having a central branch 1712, which branch is connected to a base channel 1721 of a second channel unit 1720. Each channel unit is provided with ultrasound energy from piezoelectric elements arranged under the plate 1701 at positions approximately under a portion of the base channel of each channel unit as indicated by rectangles 1716, 1726.

Figure 18:
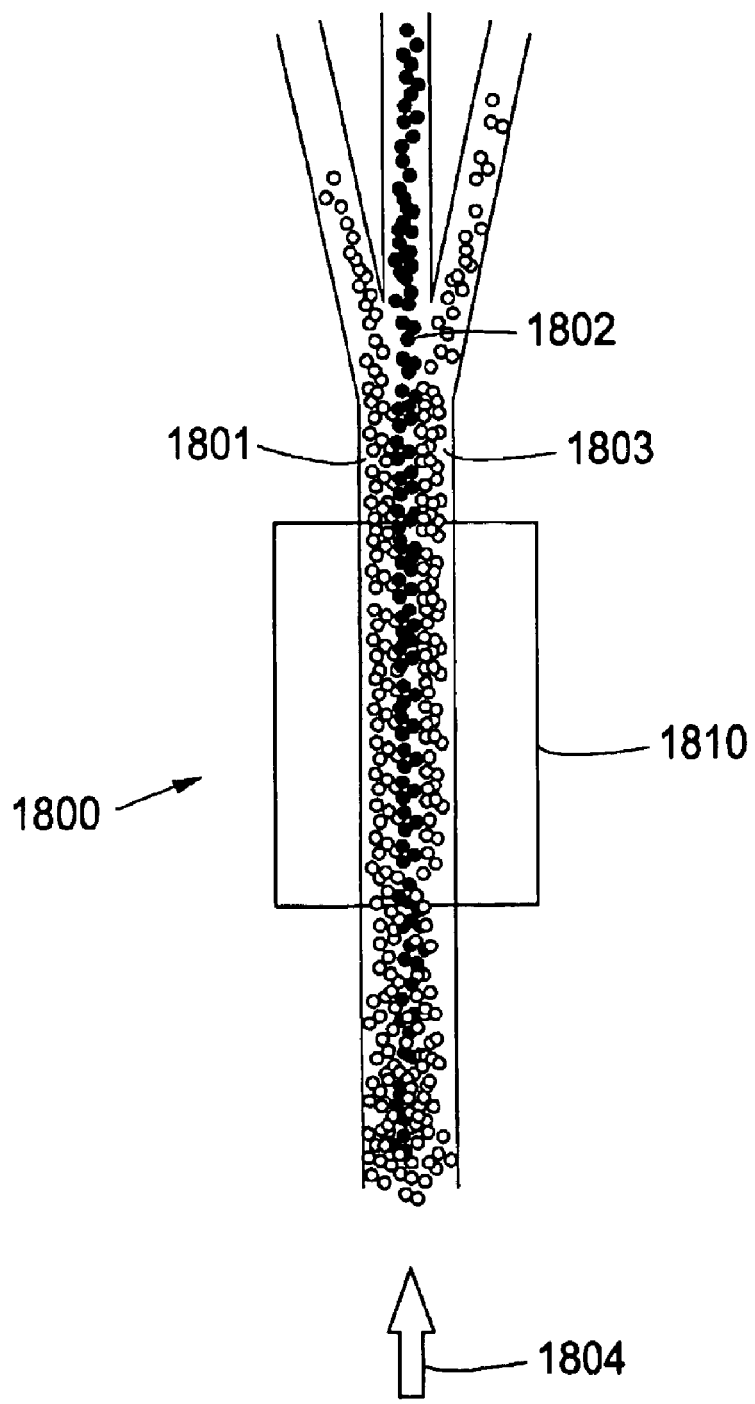
FIG. 18 illustrates a separation of two different kinds of particles with different density.

FIG. 18 show a channel unit 1800 used to separate a fluid containing two types of particles, indicated as black and white, respectively.

When fluid flows in the direction of the arrow 1804, ultrasound-standing waves are separating the particles in the channel unit into three fluid layers 1801–1803. The position of the ultrasound source is indicated by the rectangle 1810.

The described process separating two types of particles is illustrating a solution to the need within the field of medical technology to separate blood components from each other, i.e. red and white blood cells and platelets (erythrocytes, leukocytes and thrombocytes), also called the formed elements of the blood.

Known art in the field comprises mainly or solely solutions based on centrifugation. A disadvantage is that it is very difficult to obtain a complete separation of the formed elements, instead a so-called "buffy coat" is obtained. This buffy coat comprises a high concentration of thrombocytes, leukocytes and a low concentration of erythrocytes. In this context one should bear in mind that the sensitive thrombocytes have been centrifugated and subjected to high g-forces, which probably have induced an impaired function within said erythrocytes.

An embodiment of the present invention can be used to separate thrombocytes and leukocytes from erythrocytes, because they possess different densities as can be seen in table 1. Blood consists of plasma and formed elements.

TABLE 1

|  | Relative density | Standard deviation |
| --- | --- | --- |
| Particles |  |  |
| Erythrocytes | 1.09645 | 0.0018 |
| Leukocytes | 1.07–1.08 | N/A |
| Thrombocytes | 1.0645 | 0.0015 |
| Fluids |  |  |
| Plasma | 1.0269 | 0.0009 |
| Glucose 30% | 1.10 | 0 |
| Glucose 50% | 1.17 | 0 |
| Addex electrolyte | 1.18 | 0 |

Relative density. Source: Geigy Scientific Tables

Other solutions possible, iodine control agents.

As can be seen in table 1, different components have different density. The variation in density is very small for the table entries. When ordinary blood is separated, a channel unit will separate all formed elements in the same way, because their density is higher than the medium they are suspended in, i.e. the plasma.

As an alternative embodiment, the medium is modified, i.e. the plasma is modified so that its density is altered, giving the possibility to separate the different blood cells. This is achieved by adding an amount of denser liquid to the plasma and thereby dilute the plasma to a lower concentration, but with a higher density.

EXAMPLES

Take 100 ml blood with a haematocrit of 40%. This entails that 60% (=60 ml) of the blood is plasma. The plasma has a density of 1.0269. By adding 30 ml of 50% glucose solution we get according to the formula:

$$d_{tot} = \frac{v_1 * d_1 + v_2 * d_2}{v_1 + v_2}$$

where
- $v_1$ is the volume of the first fluid
- $d_1$ is the density of the first fluid
- $v_2$ is the volume of the second fluid
- $d_2$ is the density of the second fluid
- $d_{tot}$ is the density of the mix The density of the mix medium becomes 1.0746.

When this mixture is entered in an embodiment, a separation is achieved where thrombocytes and erythrocytes are directed into separate branches, because now the thrombocytes are lighter than the medium.

This is of course just an example. It is also possible to separate out leukocytes because they have a specific weight, different from the one of erythrocytes and thrombocytes. It should also be possible to separate out bacteria and virus with this method. The method can be used on all solutions except those solutions where it is impossible or otherwise inappropriate to manipulate the density of the solution. It is also possible to separate out bacteria and stem cells from cultures of the same, having them suspended in a suitable solution.

Figure 19:
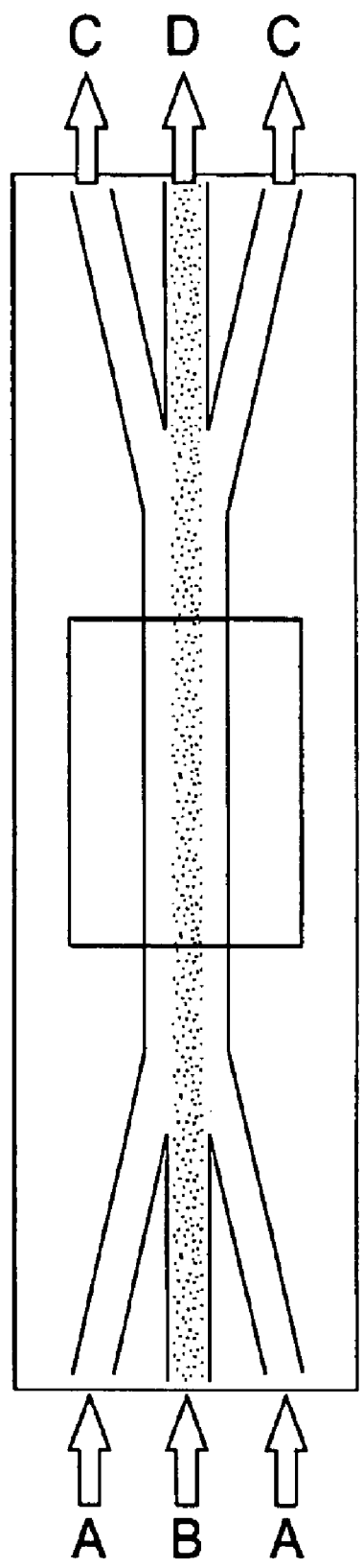
FIG. 19 illustrates a channel unit with the inlets and the outlets.
Figure 20:
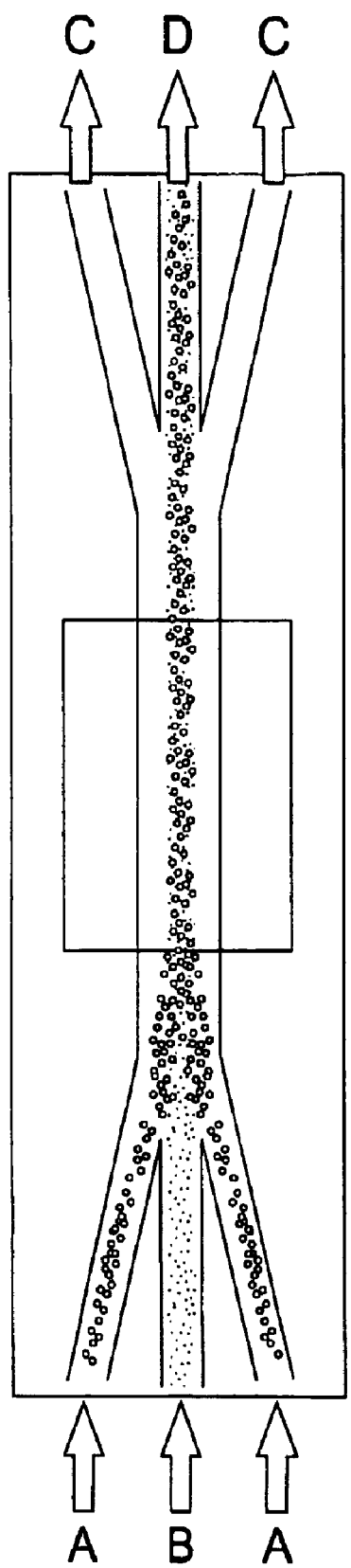
FIG. 20 illustrates the channel unit of FIG. 19 including particles.

FIG. 19 and FIG. 20 shows a channel unit with three inlets A,B,A and three outlets C,D,C. A first fluid is fed to the channel unit at both A-inlets and a second fluid is fed to the B inlet. At this microscale, the fluids will not blend.

FIG. 20 shows how particles from the fluid entered at the A-inlets are forced by the ultrasound standing wave field to migrate over to the fluid entered at the B-inlet. This type of "separation" is especially useful when the objective is to keep formed elements of the blood and discard the plasma, as in e.g. plasmapheresis, and in blood wash applications where blood cells in contaminated plasma (A) are moved to a clean solution (B) and finally blood cells in a clean medium is produced (D). The waste plasma (C) is discarded. This method will enable a highly efficient blood wash with very low amounts of washing substance needed.

Figure 21:
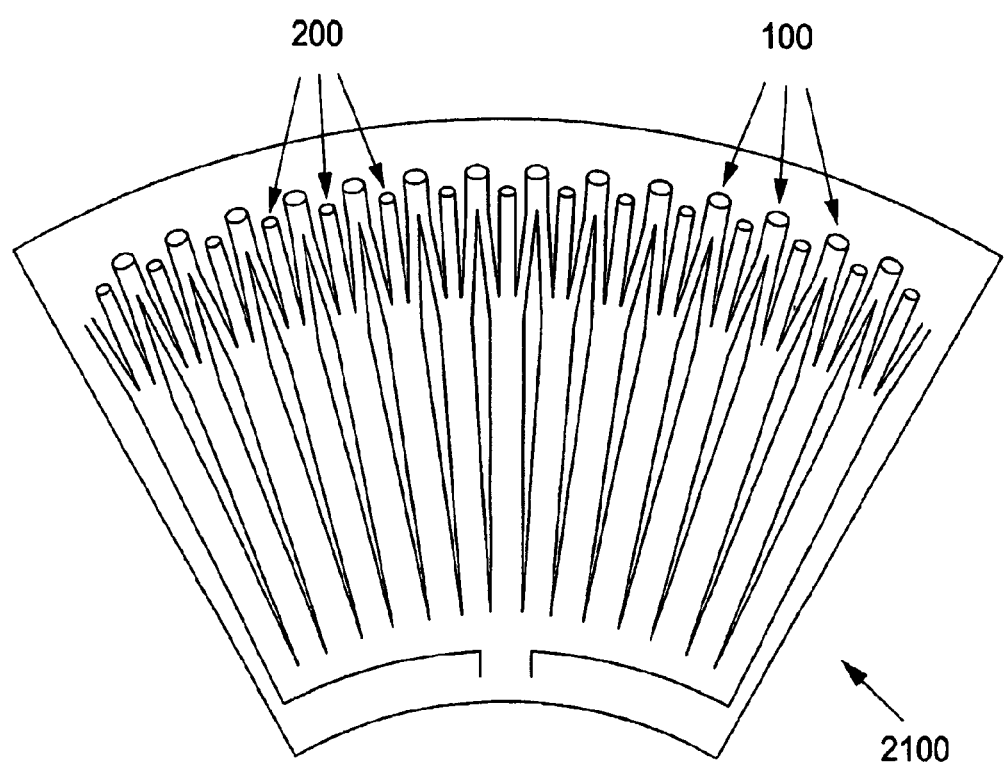
FIG. 21 shows schematically a radial arrangement of the channel units.
Figure 22:
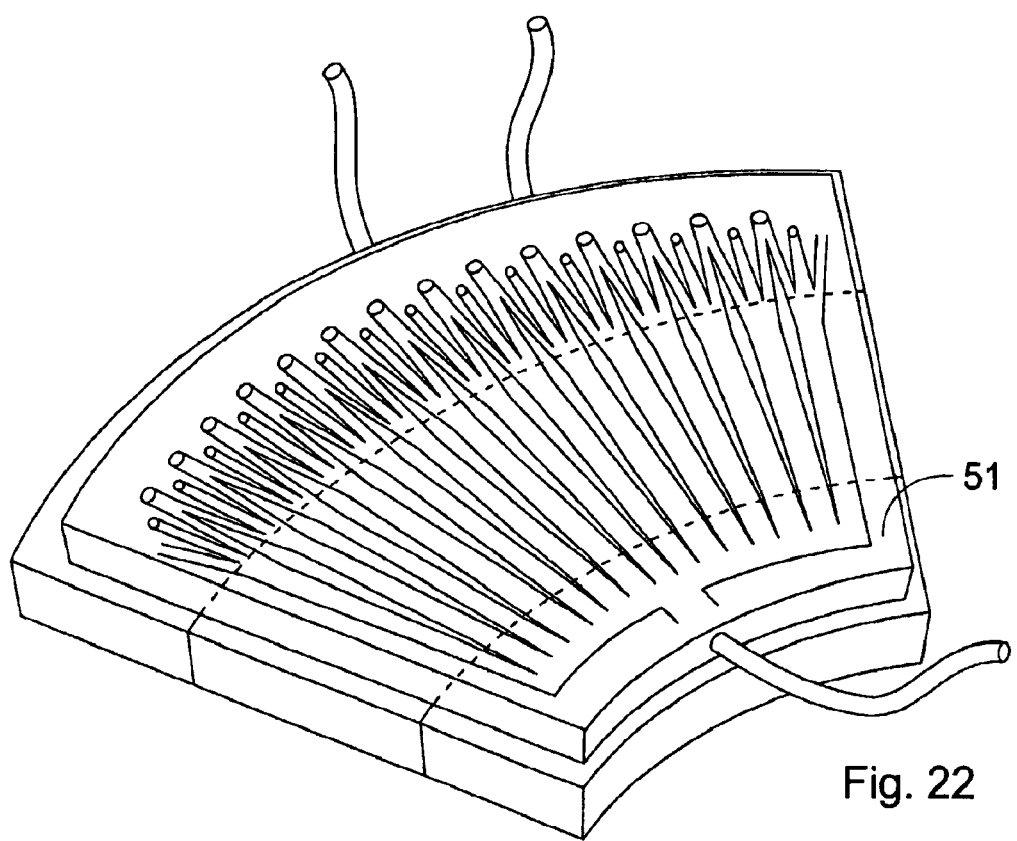
FIG. 22 shows the embodiment of FIG. 21 in perspective.

FIGS. 21 and 22 show a radial arrangement of the channel units, said arrangement being particularly advantageous when base material of the plate are circular discs or the like.

It will be appreciated by persons skilled in the art that the structure of the device according to the present invention has several advantages including ease of manufacture and solving of the problem of separating particles liable to disintegration in filtering and centrifugation processes.

What is claimed is:

1. A device for separating suspended particles from a fluid, comprising a channel unit arranged in a plate having first and second opposing great surfaces, said channel unit including a base stem channel having substantially parallel or near parallel base stem walls perpendicular to said surfaces, said base stem channel having an inlet and, opposite said inlet, a branching point connected to two or more different outlets; and oscillation means for delivering mechanical energy to a fluid in said channel unit, such that said particles are concentrated into laminar layers in the base stem channel, substantially parallel to said base stem walls, wherein said branching point is devised to separate particles, arranged in said laminar layers in a fluid flowing in said base stem channel, to said different outlets, wherein said channel unit is formed as a part of a material layer close to said first great surface, and said oscillation means are arranged in contact with said second great surface for delivering mechanical energy to said plate such that a standing wave field is created between said base stem walls.

2. A device according to claim 1, wherein said oscillation means are arranged to deliver mechanical energy in a direction perpendicular to the first and second surfaces of said plate.

3. A device according to claim 1 further comprising a control unit capable of controlling said oscillation means to deliver mechanical energy of controlled frequency and power within the ultrasound frequency band and with the frequency being so adapted to the dimensions of the channel unit that in a width of the channel, between base stem walls, an acoustic standing wave field is created.

4. A device according to claim 1, wherein a number of channel units are arranged in the same plate receiving mechanical energy from a single oscillation means allowing for integration of a large number of channel units for separation purposes on a single plate.

5. A device according to claim 1, wherein the channel unit is provided with an inlet and three outlets.

6. A device according to claim 1, wherein the plate comprises a piece of homogenous material in which said channel unit is defined.

7. A device according to claim 6, wherein the first surface of said plate is covered by a layer of glass.

8. A device according to claim 7, wherein said plate and said layer of glass are bonded together.

9. A device according to claim 1, wherein said plate is made of silicon.

10. A device according to claim 1, wherein said plate is made of plastic.

11. A device according to claim 1, wherein the branching point is shaped like a cross, and the inlet is located at the lower end of the cross base stem and the three outlets are located at the top of the cross.

12. A device according to claim 1, wherein the branching point divides the base stem into three arms with angles $\alpha 1$ and $\alpha 2$ between them, and that the value of $\alpha 1$ and $\alpha 2$ are between 0 and 90 degrees.

13. A device according to claim 1, wherein the branching point comprises the division of the base stem directly into three parallel channels divided by thin dividing walls.

14. A device according to claim 13 wherein the thin walls have a thickness of between 1 and 40 micrometer, preferably 20 micrometer.

15. A device according to claim 1, wherein the width of the channel is in the range between 60 and 1400 micrometer.

16. A device according to claim 1, wherein the width of the channel is 700 micrometer.

17. A device according to claim 1, wherein said oscillation means comprises a piezoelectric element.

18. A device according to claim 17, wherein said mechanical energy is of controlled frequency and power inside the ultrasound frequency band.

19. A device according to claim 18, wherein the electrical energy is controllable with regard to waveform, frequency and power.

20. A device according to claim 19, wherein the waveform is controllable to be one of but not limited to sinus wave, triangular wave or square wave.

21. A device according to claim 1, wherein the dimensions of the channel unit, i.e. the width and a height of the channel, the frequency of the oscillation means and a flow rate is adapted to accommodate blood as said fluid and the red blood cells as the particles to be separated from the fluid.

22. A device according to claim 1, wherein the dimensions of the channel unit, i.e. the width and a height of the channel, the frequency of the oscillation means and a flow rate is adapted to handle a fluid containing particles of biological material containing fat.

23. A device according to claim 1, wherein the channel unit is provided with three inlets and three outlets.

24. A device according to claim 22, wherein the dimensions of the channel unit, i.e. the width and a height of the channel, the frequency of the oscillation means are adapted to handle a fluid containing platelets.

25. A separator unit for use in a device according to claim 1, wherein said separator unit comprises a plate having first and second opposing great surfaces, and in that a channel unit is formed as a part of a material layer close to said first great surface, said channel unit including a base stem channel having substantially parallel or near parallel base stem walls perpendicular to said surfaces, said base stem channel having an inlet and, opposite said inlet, a branching point connected to two or more different outlets, and wherein said second surface is connectable to oscillation means for delivering mechanical energy to a fluid in said channel unit wherein a number of channels units are arranged in the same plate, for receiving mechanical energy from a single oscillation means.

26. A separator unit according to claim 25, wherein the plate comprises a piece of homogenous material in which said channel unit is defined.

27. A separator unit according to claim 26, wherein said homogenous material is plastic.

28. A separator unit according to claim 26, wherein said homogeneous material is silicon.

29. A separator unit according to claim 26, wherein the first surface of said plate is covered by a sealing layer which makes it possible to visually inspect a separation process in said channel.

30. A separator unit according to claim 29, wherein the sealing layer is made of glass.

31. A separator unit according to claim 30, wherein said plate and said layer of glass are bonded together.

32. A method for separating particles from fluids using ultrasound, laminar flow, and stationary wave effects comprising the steps of:

feeding a fluid to a separator unit comprising a plate having first and second opposing great surfaces and a channel unit formed as a part of a material layer close to said first surface, forcing the fluid to a substantially laminar flow in a flow direction;

applying an ultrasound oscillating wave field to said second surface, thereby subjecting said flow to an ultrasound stationary wave field during its flow past a distance in said channel unit, forcing said particles to a non-uniform distribution in a separation direction parallel to said surfaces and perpendicular to the flow direction; and separating said second laminar flow into a first and a second separated flow in such a way that the concentration of particles is higher in the first separated flow than in the second separated flow.

33. The method according to claim 32, wherein said ultrasound oscillating wave field is given a frequency adapted to a width of the channel unit, such that vibrations in the plate give rise to said wave field parallel with the plate.

34. The method according to claim 32, wherein said ultrasound oscillating wave field is applied perpendicular to said surfaces of the plate.

35. The method according to claim 32, further comprising the step of separating out particles of biological material containing fat from a fluid.

36. The method according to claim 32, further comprising the step of separating particles from blood.

37. The method as recited in claim 32, further comprising the step of separating out bacteria from a fluid.

38. The method as recited in claim 32, further comprising the step of separating out stem cells from a fluid.

39. The method as recited in claim 32, further comprising the step of separating out platelets from a fluid.

40. The method as recited in claim 32, further comprising the step of adding a solution to the original fluid, said solution having a different density than the original fluid, with the purpose of altering the density of the fluid from which particles are to be separated.

41. The method according to claim 32, wherein the method is repeated in a number of stages.

42. The method according to claim 41, wherein new fluid is introduced before the steps are repeated.

43. The method according to claim 32, further comprising the step of controlling the power fed to the ultrasound stationary wave field by means of controlling the electrical energy with regard to waveform, frequency and power to a piezoelectric element transmitting its mechanical energy to the fluid and its surroundings.

* * * * *